(12) United States Patent
Yoshimura et al.

(10) Patent No.: US 8,273,847 B2
(45) Date of Patent: Sep. 25, 2012

(54) MEDICAL ADHESIVE

(75) Inventors: Tetsuji Yoshimura, Kyoto (JP); Tetsuya Yamada, Kyoto (JP); Takehisa Matsuda, Mino (JP)

(73) Assignee: Sanyo Chemical Industries, Ltd, Kyoto-shi (JP)

( * ) Notice: Subject to any disclaimer, the term of this patent is extended or adjusted under 35 U.S.C. 154(b) by 337 days.

(21) Appl. No.: 10/594,627

(22) PCT Filed: Mar. 23, 2005

(86) PCT No.: PCT/JP2005/005274
§ 371 (c)(1),
(2), (4) Date: Jul. 16, 2007

(87) PCT Pub. No.: WO2005/092404
PCT Pub. Date: Oct. 6, 2005

(65) Prior Publication Data
US 2007/0282093 A1 Dec. 6, 2007

(30) Foreign Application Priority Data
Mar. 29, 2004 (JP) .................................. 2004-094251

(51) Int. Cl.
*A61L 26/00* (2006.01)
*C08G 18/73* (2006.01)
*C08G 18/77* (2006.01)
*C08K 5/13* (2006.01)
*C09J 175/08* (2006.01)

(52) U.S. Cl. ........ 528/111; 523/118; 524/323; 524/342; 524/345; 524/736; 524/738; 528/59; 528/70; 528/76; 528/905; 560/158; 560/161; 602/52

(58) Field of Classification Search .................. 523/111, 523/118; 524/323, 342, 345, 736, 738; 528/59, 528/70, 905, 76; 560/25, 26, 30, 115, 158, 560/161; 602/52
See application file for complete search history.

(56) References Cited

U.S. PATENT DOCUMENTS

| | | | |
|---|---|---|---|
| 5,527,266 A | 6/1996 | Hiraishi et al. | |
| 2003/0225239 A1* | 12/2003 | Nakamura et al. | 528/59 |
| 2004/0033251 A1* | 2/2004 | Sparer et al. | 424/425 |
| 2005/0060022 A1* | 3/2005 | Felt et al. | 623/1.15 |

FOREIGN PATENT DOCUMENTS

| | | |
|---|---|---|
| GB | 2399345 A | 9/2004 |
| JP | 1-227762 A | 9/1989 |
| JP | 7-11124 A | 1/1995 |
| WO | WO 03/051952 A1 | 6/2003 |

* cited by examiner

*Primary Examiner* — Rabon Sergent
(74) *Attorney, Agent, or Firm* — Westerman, Hattori, Daniels & Adrian, LLP

(57) ABSTRACT

A medical adhesive comprises a hydrophilic urethane prepolymer (UP) obtained by reacting a fluorine-containing non-aromatic polyisocyanate component (A) and a polyol component (B) having a hydrophilic polyol (B1), and a phenolic radical scavenger (PRS). The content of (PRS) is preferably 0.01 to 3% by weight based on the weight of (UP). The content of oxyethylene groups in (B) is preferably 30 to 100% by weight based on the weight of the oxyalkylene groups in (B). Preferably, (B) is a mixture of a random copolymer obtained by addition of ethylene oxide and propylene oxide to diols and polypropylene glycol. The content of isocyanate groups in the medical adhesive is 1 to 10% by weight based on the weight of (UP). The medical adhesive is suitable for bonding body tissues, such as lung, artery and heart in particular.

8 Claims, 1 Drawing Sheet

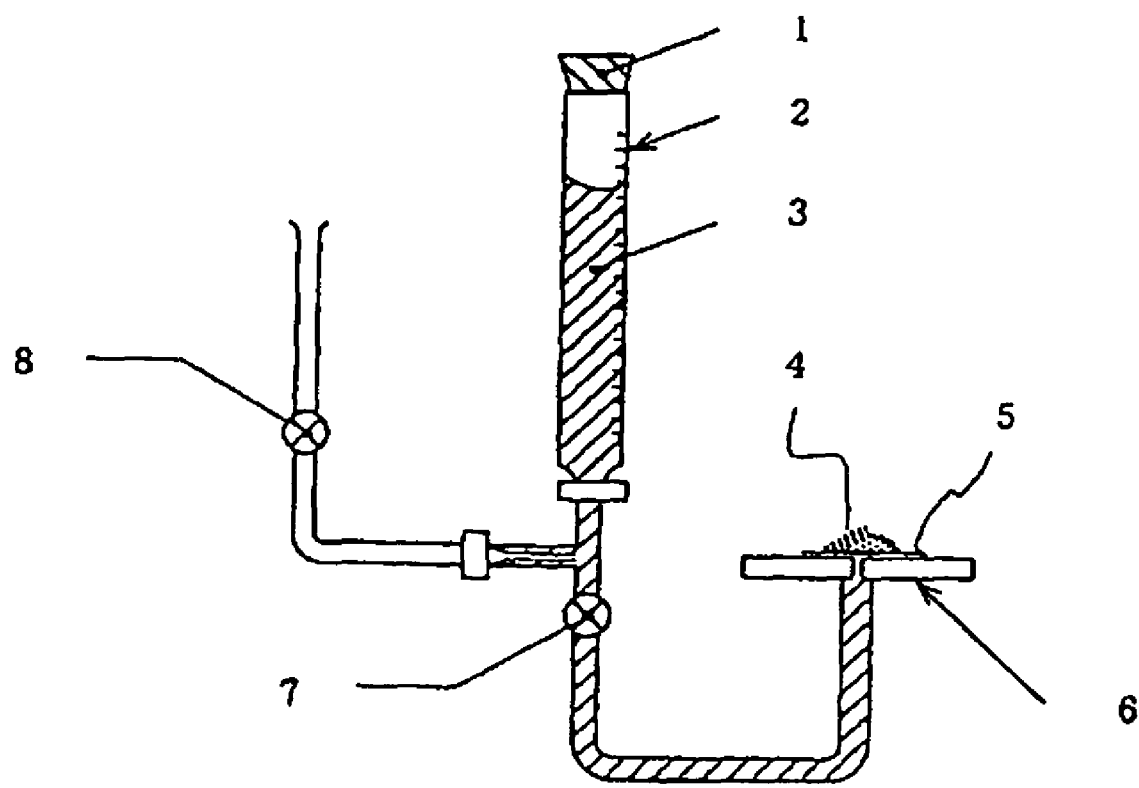

MEDICAL ADHESIVE

TECHNICAL FIELD

The present invention relates to a medical adhesive. More particularly, the invention relates to a medical adhesive suitable for bonding body tissues which moves in the interior of the body, such as especially artery, heart, and lung. Moreover, the present invention relates to a medical adhesive suitable as a hemostatic sealant to stop bleeding from blood vessel, heart, and the like (blood spurting in a surgical operation, and the like).

BACKGROUND ART

Because the safety to the human body is valued in the medical adhesive, it should be specifically considered to select the raw materials. For example, when an aromatic polyisocyanate, which does not contain a fluorine atom, is used as a polyisocyanate component, an unreacted aromatic polyisocyanate remaining in the urethane prepolymer reacts with water in the body fluid such as blood to turn into an aromatic amine which has high possibility of mutagenicity. Therefore, using the aromatic polyisocyanate as a raw material for the medical adhesive has a problem from the viewpoint of safety.

Moreover, when an aliphatic polyisocyanate or an alicyclic polyisocyanate is used as a polyisocyanate component, because the reactivity of an isocyanate group in the urethane prepolymer is low, there is a problem of not obtaining a practical curing rate at the temperature in the vicinity of the body temperature.

Then, as a medical adhesive with safety against mutagenicity etc. and practical reactivity (curing rate), a medical adhesive comprising a fluorine-containing hydrophilic urethane prepolymer terminated by an isocyanate group obtained by the reaction of a fluorine-containing polyisocyanate and a hydrophilic polyether polyol has been developed (Japanese Kokai Publication Hei-1-227762 (corresponding patent application: U.S. Pat. No. 4,994,542A, and the like), and International Publication WO03/051952 (corresponding patent application: A.U. Patent No. 2002343788A1, and the like)).

This medical adhesive comprising a fluorine-containing hydrophilic urethane prepolymer terminated by an isocyanate group reacts with water in the body fluid such as blood and lymph to form an amine and carbon dioxide, and this amine further reacts with the fluorine-containing hydrophilic urethane prepolymer terminated by an isocyanate group and promotes molecular weight-increasing process (polymerization), and the adherend can be bonded. At this time, the urethane prepolymer foams by the generated carbon dioxide and becomes a spongelike cured product (product cured by the reaction with water). And, this cured product (foam) is excellent in adhesive strength and flexibility.

A cured product (the foam product obtained by the reaction with water), which is obtained by curing a conventional medical adhesive, has such a problem as easily deteriorate and decompose with the passage of time and can not be said to be excellent in the duration of adhesive strength. For example, part or all of the cured product (foam sheet) obtained by applying this conventional medical adhesive (comprising the fluorine-containing hydrophilic urethane prepolymer terminated by an isocyanate group) on a glass board and soaking the board in water to cure the adhesive becomes viscous liquid (deteriorates/decomposes) on several days at 25 to 40° C., and the adhesive strength might decrease greatly.

SUMMARY OF THE INVENTION

That is, the object of the present invention is to provide a medical adhesive excellent in the duration of adhesive strength.

The present inventor found that the phenomenon that the cured product obtained from an adhesive deteriorates/decomposes and the adhesive strength decreases greatly could not been seen when a fluorine-free aromatic isocyanate (for example, 2,4- or 2,6-tolylenediisocyanate (TDI) or 2,4'- or 4,4'-diphenylmethane diisocyanate (MDI), and the like) is used as a polyisocyanate component, and was a specific phenomenon that occurred only when the fluorine-containing nonaromatic isocyanate compound was used, and our further intensive study revealed that the above-mentioned problem could be solved by using a specific radical scavenger (a phenolic radical scavenger), resulting in the present invention.

That is, the feature of the medical adhesive of the present invention is that it comprises a hydrophilic urethane prepolymer (UP) obtained by reacting a fluorine-containing nonaromatic polyisocyanate component (A) and a polyol component (B) having a hydrophilic polyol (B1) as the essential component, and a phenolic radical scavenger (PRS).

DETAILED DESCRIPTION OF THE INVENTION

In the present invention, the fluorine-containing nonaromatic polyisocyanate component (A) has a fluorine-containing nonaromatic polyisocyanate (A1) as the essential component, but may contain a fluorine-free polyisocyanate (A2) and/or a fluorine-containing aromatic polyisocyanate (A3), and the like as an arbitrary component.

Here, from the viewpoint of the safety against mutagenicity etc. and the reactivity with water (curing rate), it is preferable that the fluorine-free polyisocyanate (A2) and the fluorine-containing aromatic polyisocyanate (A3) are not contained. It is acceptable, however, that (A2) and/or (A3) are contained as long as there are no problems in the reactivity and safety in order to adjust the reactivity (curing rate), adhesive strength, and the like.

As the fluorine-containing nonaromatic polyisocyanate (A1), fluorine-containing aliphatic diisocyanates (A11) having 5 to 22 carbon atoms (this number does not take account of carbon atom(s) in an isocyanate group, hereinafter the same shall apply), fluorine-containing alicyclic diisocyanates (A12) having 8 to 19 carbon atoms, fluorine-containing poly(3 to 6 in valence) isocyanates (A13) having 15 to 66 carbon atoms, and the like can be used.

The fluorine-containing aliphatic diisocyanates (A11) having 5 to 22 carbon atoms include those represented by OCN—Rf—NCO, those represented by OCN—$CH_2$—Rf—$CH_2$—NCO, and the like. In both formulae, Rf represents a perfluoroalkylene group having 1 to 20 carbon atoms, which may contain an ether bond.

Those represented by OCN—Rf—NCO include difluoromethylene diisocyanate, perfluorodimethylene diisocyanate, perfluorotrimethylene diisocyanate, perfluoroeicosa diisocyanate, bis(isocyanatoperfluoroethyl)ether, bis(isocyanatoperfluoroisopropyl)ether and the like.

Those represented by OCN—$CH_2$—Rf—$CH_2$—NCO include bis(isocyanatomethyl)difluoromethane, bis(isocyanatomethyl)perfluoroethane, bis(isocyanatomethyl)perfluoropropane, bis(isocyanatomethyl)perfluorobutane, bis(isocyanatomethyl)perfluoropentane, bis(isocyanatomethyl)

perfluorohexane, bis(isocyanatomethyl)perfluoroeicosane, bis(isocyanatomethyl perfluoroethyl)ether and the like.

The fluorine-containing alicyclic diisocyanates (A12) having 8 to 19 carbon atoms include diisocyanatoperfluorocyclohexane, bis(isocyanatomethyl)perfluorocyclohexane, bis(isocyanatomethyl)perfluorodimethylcyclohexane, bis(isocyanatoperfluorocyclohexyl), bis(isocyanatoperfluorocyclohexyl)perfluoropropane, bis(isocyanatomethylperfluorocyclohexyl)perfluoropropane and the like.

The fluorine-containing poly(3 to 6 in valence) isocyanates (A13) having 15 to 66 carbon atoms include the nulate body of the above-mentioned diisocyanate, tris(isocyanatoperfluorophenyl)methane, tris(isocyanatotetrafluorocyclohexyl) methane and the like.

Further, the position of the isocyanate group in the fluorine-containing nonaromatic polyisocyanate (A1) is preferably the position where the steric hindrance is a little, and more preferably the terminal position where the steric hindrance is small from the viewpoints of reactivity with the polyol component (B) and reactivity with blood and body fluid etc., and the like viewpoints.

The fluorine-containing nonaromatic polyisocyanate (A1) may be one kind or a mixture of two kinds or more.

Moreover, among the fluorine-containing nonaromatic polyisocyanates (A1), those having two isocyanate groups are preferable from the viewpoint of side reactions such as the crosslinking reaction, and the like viewpoints.

Among the fluorine-containing nonaromatic polyisocyanates (A1), the fluorine-containing aliphatic polyisocyanates (A11) and the fluorine-containing alicyclic polyisocyanates (A12) are preferable, fluorine-containing aliphatic polyisocyanates represented by $OCN-CH_2-Rf-CH_2-NCO$ are more preferable, and bis(isocyanatomethyl)perfluoropropane, bis(isocyanatomethyl)perfluorobutane, bis(isocyanatomethyl)perfluoropentane, and bis(isocyanatomethyl)perfluorohexane are particularly preferable, from the viewpoint of the safety against mutagenicity etc., and the like viewpoints.

As the fluorine-free polyisocyanates (A2), fluorine-free aliphatic polyisocyanates (A21) having 1 to 22 carbon atoms, fluorine-free alicyclic polyisocyanates (A22) having 6 to 19 carbon atoms, fluorine-free aromatic aliphatic polyisocyanates (A23) having 8 to 16 carbon atoms, fluorine-free aromatic polyisocyanates (A24) having 6 to 19 carbon atoms, modified products thereof (A25), and the like can be used.

The fluorine-free aliphatic polyisocyanates (A21) include tetramethylene diisocyanate, hexamethylene diisocyanate (HDI), 2,2,4-trimethylhexamethylene diisocyanate, lysine diisocyanate and the like.

The fluorine-free alicyclic polyisocyanates (A22) include isophorone diisocyanate (IPDI), dicyclohexylmethane-4,4'-diisocyanate (hydrogenated MDI), cyclohexylene diisocyanate, methylcyclohexylene diisocyanate (hydrogenated TDI) and the like.

The fluorine-free aromatic aliphatic polyisocyanates (A23) include m- or p-xylylene diisocyanate (XDI), α,α,α',α'-tetramethylxylylene diisocyanate (TMXDI) and the like.

The fluorine-free aromatic polyisocyanates (A24) include 1,3- or 1,4-phenylene diisocyanate (PDI), 2,4- or 2,6-tolylenediisocyanate (TDI), 2,4'- or 4,4'-diphenylmethane diisocyanate (MDI), crude MDI and the like.

These modified products (A25) include modified HDI (such as urethane-modified HDI, carbodiimide-modified HDI and trihydrocarbylphosphate-modified HDI), modified MDI (such as urethane-modified MDI and carbodiimide-modified MDI), modified TDI (such as urethane-modified TDI and carbodiimide-modified TDI), and the like.

The fluorine-free polyisocyanate (A2) may be one kind or a mixture of two kinds or more.

Among these polyisocyanates (A2), the fluorine-free aromatic polyisocyanates (A24) are preferable from the viewpoint of reactivity and the like, and MDI and TDI are more preferable. When the fluorine-free polyisocyanate (A2) is used, the content (% by weight) of (A2) is preferably from 0.1 to 20, more preferably from 0.2 to 10, and particularly preferably from 0.3 to 5, based on the weight of the fluorine-containing nonaromatic polyisocyanate (A1) from the viewpoint of the safety against mutagenicity etc., and the like viewpoints.

As the fluorine-containing aromatic polyisocyanates (A3), fluorine-containing aromatic polyisocyanates (A31) wherein part or all of hydrogen atoms in the aromatic ring in the fluorine-free aromatic polyisocyanates (A24) are substituted with fluorine atoms, fluorine-containing aromatic polyisocyanates (A32) wherein part or all of hydrogen atoms in the aromatic ring are substituted with fluoroalkyl groups and/or fluoroalkylene groups, fluorine-containing aromatic polyisocyanates (A33) wherein part or all of hydrogen atoms in the aromatic ring are substituted with fluorine atoms and fluoroalkyl groups and/or fluoroalkylene groups, and the like are used.

The fluorine-containing aromatic polyisocyanates (A31) include 1,3- or 1,4-perfluorophenylene diisocyanate, 1,3,5,6- or 1,3,4,5-tetrafluoro-2,4- or 2,6-tolylenediisocyanate, tetrafluoro-2,4'- or 4,4'-diphenylmethane diisocyanate and the like.

The fluorine-containing aromatic polyisocyanates (A32) include trifluoromethylphenylene-1,3- or 1,4-perfluoro diisocyanate, 2,4'- or 4,4'-diphenyldifluoromethane diisocyanate and the like.

The fluorine-containing aromatic polyisocyanates (A33) include 2,4- or 2,6-perfluorotolylenediisocyanate, 2,4'- or 4,4'-perfluorodiphenylmethane diisocyanate, and the like.

The fluorine-containing aromatic polyisocyanate (A3) may be one kind or a mixture of two kinds or more.

Among these polyisocyanates (A3), the fluorine-containing aromatic polyisocyanates (A31) wherein at least part or all of hydrogen atoms in the aromatic ring are substituted with fluorine atoms, and the fluorine-containing aromatic polyisocyanates (A33) are preferable and the fluorine-containing aromatic polyisocyanates (A33) are more preferable from the reactivity and the like viewpoints.

When the fluorine-containing polyisocyanate (A3) is used, the content (% by weight) of (A3) is preferably from 0.1 to 5, more preferably from 0.2 to 3, and particularly preferably from 0.3 to 2, based on the weight of the fluorine-containing nonaromatic polyisocyanate (A1) from the viewpoint of the safety against mutagenicity etc., and the like viewpoints.

As the polyol component (B), though the hydrophilic polyol (B1) is essential, low-hydrophilic other polyols (B2) may be included.

The hydrophilic polyols (B1) include a polyol which contains an oxyethylene group and wherein the content of oxyethylene groups is at least 30% by weight based on the weight of the oxyalkylene group, and as the hydrophilic polyols (B1), a polyether polyol (B1-1) containing an oxyethylene group, a polyester polyol (B1-2) comprising the polyether polyol (B1-1) containing an oxyethylene group as an essential constitutional unit, and the like can be used.

The oxyalkylene groups include oxyalkylene groups having 2 to 8 carbon atoms (such as oxyethylene, oxypropylene, oxybutylene, and oxyphenylethylene group), and the like.

As the polyether polyol (B1-1) containing an oxyethylene group, adducts of ethylene oxide, or co-adducts of ethylene oxide and alkylene oxide having 3 to 8 carbon atoms (such as 1,2- or 1,3-propylene oxide, 1,2-, 1,3-, 2,3-, or 1,4-butylene oxide, and styrene oxide) to compounds having at least two active hydrogens can be used. In case of co-adducts, the adduct form may be any of random, block, and these combinations, but random is preferable.

As the alkylene oxide having 3 to 8 carbon atoms, 1,2-propylene oxide is preferable.

As the compound having at least two active hydrogens, water, diols, polyols of 3 to 8 in valence, dicarboxylic acids, polycarboxylic acids of 3 to 4 in valence, monoamines, polyamines, polythiols, and the like can be used.

Further, when a compound having two active hydrogens is used, a bivalent hydrophilic polyol is obtained, and when a compound having three more active hydrogens is used, a hydrophilic polyol of three or more in valence is obtained.

As the diol, alkylene glycols having 2 to 30 carbon atoms (such as ethylene glycol, 1,2-propylene glycol, 1,3-propylene glycol, 1,4-butanediol, 1,6-hexanediol, octanediol, decanediol, dodecanediol, tetradecanediol, neopentyl glycol, and 2,2-diethyl-1,3-propanediol); alicyclic diols having 6 to 24 carbon atoms (such as 1,4-cyclohexane dimethanol and hydrogenated bisphenol A); bisphenols having 15 to 30 carbon atoms (such as bisphenol A, bisphenol F, and bisphenol S); dihydroxybenzenes (such as catechol and hydroquinone); and the like are used.

As the polyol of 3 to 8 in valence, aliphatic polyhydric alcohols having 3 to 8 carbon atoms (such as glycerin, trimethylolethane, trimethylolpropane, pentaerythritol, sorbitan, diglycerin, and sorbitol), and the like are used.

As the dicarboxylic acid, alkane dicarboxylic acids having 4 to 32 carbon atoms (such as succinic acid, adipic acid, sebacic acid, dodecenylsuccinic acid, azelaic acid, sebacic acid, dodecane dicarboxylic acid, octadecane dicarboxylic acid, dodecyl succinic acid, and octadecyl succinic acid); alkene dicarboxylic acids having 4 to 32 carbon atoms (such as maleic acid, fumaric acid, citraconic acid, mesaconic acid, dimmer acid, dodecenylsuccinic acid, and pentadecenylsuccinic acid); aromatic dicarboxylic acids having 8 to 20 carbon atoms (such as phthalic acid, isophthalic acid, terephthalic acid, and naphthalenedicarboxylic acid); and the like are used. Besides these, acid anhydrides of dicarboxylic acids (such as maleic anhydride and phthalic anhydride) and lower alkyl (having 1 to 4 carbon atoms) esters (such as methyl ester, ethyl ester, isopropyl ester, and t-butyl ester), and the like can also used.

As the polycarboxylic acid of 3 to 4 in valence, aromatic polycarboxylic acids having 9 to 20 carbon atoms (such as trimellitic acid and pyromellitic acid), and the like are used. Besides these, acid anhydrids of polycarboxylic acids (such as trimellitic anhydride and pyromellitic anhydride) and lower alkyl (having 1 to 4 carbon atoms) esters (such as methyl ester, ethyl ester, and isopropyl ester), and the like can also be used.

As the monoamine, ammonia and aliphatic primary amines having 1 to 20 carbon atoms {such as alkyl amines having 1 to 20 carbon atoms (such as methylamine, ethylamine, propylamine, hexylamine, dodecylamine, and eicosylamine)}; alicyclic amines having 4 to 15 carbon atoms (such as piperidine, aminocyclohexane, isophorone monoamine, and 4-methylene dicyclohexane monoamine); aromatic ring-containing aliphatic amines having 6 to 15 carbon atoms (such as aniline); and the like are used.

As the polyamine, aliphatic polyamines having 2 to 18 carbon atoms {such as alkylene diamines having 2 to 12 carbon atoms (such as ethylene diamine, propylene diamine, trimethylene diamine, hexamethylene diamine, N,N'-diethylethylene diamine, and undecylene diamine), and polyalkylene (having 2 to 6 carbon atoms) polyamines (such as diethylenetriamine, dipropylenetriamine, triethylenetetramine, and pentaethylenehexamine)}; alicyclic polyamines having 4 to 15 carbon atoms (such as 1,3-diaminocyclohexane, isophoronediamine, and 4,4'-methylenedicyclohexanediamine); heterocyclic polyamines having 4 to 15 carbon atoms (such as piperazine, N-aminoethyl piperazine, 1,4-diaminoethyl piperazine, and N-aminoethyl pyridine); and the like are used.

As the polythiol, dithiols having 2 to 24 carbon atoms (such as ethanedithiol, 1,4-butanedithiol, and 1,6-hexanedithiol), polythiols of 3 to 6 in valence and having 5 to 3,000 carbon atoms (trade name; Capcure 3800 (manufactured by Japan Epoxy Resins Co., Ltd.), and polyvinyl thiol), and the like are used.

Besides these compounds having at least two active hydrogens, amino acids, oxycarboxylic acids, amino alcohols, and the like can also be used.

These compounds having at least two active hydrogens may be one kind or a mixture of two kinds or more.

Among these compounds having at least two active hydrogens, water and diols are preferable, water and alkylene glycols are more preferable, and water and alkylene glycols having 2 to 4 carbon atoms are particularly preferable.

Suitable examples of the polyether polyols (B1-1) containing an oxyethylene group include adducts of ethylene oxide to diols (such as an adduct of ethylene oxide to ethylene glycol and an adduct of ethylene oxide to propylene glycol), co-adducts of ethylene oxide and alkylene oxide having 3 to 8 carbon atoms to diols (such as a random or block co-adduct of ethylene oxide and propylene oxide to ethylene glycol and a random or block co-adduct of ethylene oxide and butylene oxide to ethylene glycol), and the like.

Among these, adducts of ethylene oxide to diols and co-adducts of ethylene oxide and propylene oxide to diols are preferable from the viewpoint that the reactivity with water quickens and the adhesive strength and the like become more excellent, and the like, and co-adducts of ethylene oxide and propylene oxide to diols are particularly preferable.

These polyether polyols (B1-1) may be one kind or a mixture of two kinds or more.

The equivalent weight of the hydroxyl group (the number average molecular weight per one hydroxyl group) in the polyether polyols (B1-1) is preferably from 50 to 5,000, more preferably from 100 to 4,000, and particularly preferably from 200 to 3,000. Within this range, the adhesive strength and the like become further excellent.

The equivalent weight of the hydroxyl group is measured according to JIS K1557-1970 "6.4 Hydroxyl value."

As the polyester polyol (B1-2) comprising a polyether polyol (B1-1) as an essential constitutional unit, polyesters of the polyether polyol (B1-1) with the above-mentioned dicarboxylic acid, an anhydride of the dicarboxylic acid and/or a lower alkyl ester of the dicarboxylic acid, and the like are used. The terminus or termini of these polyesters are hydroxyl group(s).

Further, as part of the dicarboxylic acid, the anhydride of the dicarboxylic acid and/or the lower alkyl ester of the dicarboxylic acid, a polycarboxylic acid, an anhydride of a polycarboxylic acid and a lower alkyl ester of a polycarboxylic acid, and the like may also be used, and when these are used, the amount (% by mole) of these used are preferably from 0.1 to 10, more preferably from 0.1 to 5, and particularly preferably from 0.1 to 2, based on the total number of moles of all of the carboxylic acids, the anhydrides of the carboxylic acid and the lower alkyl esters of the carboxylic acid. Within this range, the adhesive strength and the like become further excellent.

Suitable examples of polyester polyols (B1-2) include polyester diols of adducts of ethylene oxide to diols (such as an adduct of ethylene oxide to ethylene glycol and an adduct of ethylene oxide to propylene glycol) with dicarboxylic acids (such as adipic acid, sebacic acid, maleic acid, and phthalic acid), anhydrides of the dicarboxylic acid and/or lower alkyl esters of the dicarboxylic acid (such as methyl ester and ethyl ester of a dicarboxylic acid); polyester diols of co-adducts of ethylene oxide and alkylene oxide having 3 to 8 carbon atoms to diols (such as a random or block co-adduct of ethylene oxide and 1,2- or 1,3-propylene oxide to ethylene glycol and a random or block co-adduct of ethylene oxide and 1,4-butylene oxide to propylene glycol) with dicarboxylic acids, anhydrides of the dicarboxylic acid and/or lower alkyl esters of the dicarboxylic acid; and the like.

Among these, polyester diols of adducts of ethylene oxide to diols with dicarboxylic acids, anhydrides of the dicarboxylic acid and/or lower alkyl esters of the dicarboxylic acid, and polyester diols of co-adducts of ethylene oxide and propylene oxide to diols with dicarboxylic acids, anhydrides of the dicarboxylic acid and/or lower alkyl esters of the dicarboxylic acid are preferable, and polyester diols of adducts of ethylene oxide to diols with dicarboxylic acids, anhydrides of the dicarboxylic acid and/or lower alkyl esters of the dicarboxylic acid are more preferable, from the adhesive strength and the like viewpoints.

These polyester polyols (B1-2) may be one kind or a mixture of two kinds or more.

The equivalent weight of the hydroxyl group in the polyester polyol (B1-2) is preferably from 50 to 5,000, more preferably from 100 to 4,000, and particularly preferably from 200 to 3,000. Within this range, the adhesive strength and the like become further excellent.

The content (% by weight) of oxyethylene groups in the hydrophilic polyol (B1) is 30 to 100, preferably from 40 to 95, and more preferably from 50 to 90, based on the total weight of the oxyethylene groups and the oxyalkylene groups having 3 to 8 carbon atoms. Within this range, the adhesive strength and the like become further excellent.

The equivalent weight of the hydroxyl group in the hydrophilic polyol (B1) is preferably from 50 to 5,000, more preferably from 100 to 4,000, and particularly preferably from 200 to 3,000. Within this range, the adhesive strength and the like become further excellent.

As the hydrophilic polyether (B1), co-adducts of ethylene oxide and propylene oxide to water, ethylene glycol and/or propylene glycol, wherein the number average molecular weight (Mn) is 2,000 to 6,000 and the content of oxyethylene groups is 60 to 95% by weight, are preferably used.

The low-hydrophilic other polyols (B2), besides diols and polyols of 3 to 6 in valence, include a polyol which contains an oxyalkylene group and wherein the content of oxyethylene groups is less than 30% by weight based on the weight of the oxyalkylene group, and as the low-hydrophilic other polyols (B2), a polyether polyol (B2-1), a polyester polyol (B2-2) comprising the polyether polyol (B2-1) as an essential constitutional unit, a polyester polyol (B2-3) not containing an oxyethylene group and an oxyalkylene group having 3 to 8 carbon atoms, and the like can be used.

As the polyether polyol (B2-1), (co-)adducts of an alkylene oxide having 3 to 8 carbon atoms to, and co-adducts of ethylene oxide and an alkylene oxide having 3 to 8 carbon atoms to a compound having at least two active hydrogens, and the like can be used. However, the content of oxyethylene groups is less than 30% by weight based on the total weight of the oxyethylene groups and the oxyalkylene groups.

Suitable examples of the polyether polyols (B2-1) include polypropylene glycol (an adduct of 1,2- or 1,3-propylene oxide to propylene glycol), adducts of ethylene oxide to polyalkylene glycols (such as a block adduct of ethylene oxide and propylene oxide to ethylene glycol or propylene glycol, in which the content of ethylene oxides is 5 to 45% by weight), random copolymers of propylene oxide and ethylene oxide (such as a random adduct of ethylene oxide and propylene oxide to ethylene glycol or propylene glycol, in which the content of ethylene oxides is 10 to 25% by weight), polytetramethylene glycol (an adduct of 1,2-, 1,3-, 2,3-, or 1,4-butylene oxide to 1,4-butylene glycol), copolymers of 1,4-butylene oxide and ethylene oxide (such as a block or random adduct of 10 to 25% by weight of ethylene oxide and 75 to 95% by weight of 1,4-butylene oxide to ethylene glycol or butylenes glycol, in which the content of ethylene oxides is 10 to 25% by weight), and the like.

Among these, the adducts of ethylene oxide to polypropylene glycol (the content of ethylene oxides is 5 to less than 30% by weight) are preferable and the adducts of ethylene oxide to polypropylene glycol (the content of ethylene oxides is 15 to less than 30% by weight) are more preferable from the hydrophilicity and the like viewpoints.

These polyether polyols (B2-1) may be one kind or a mixture of two kinds or more.

The equivalent weight of the hydroxyl group in the polyether polyol (B2-1) is the same as that of the polyether polyol (B1-1).

As the polyester polyol (B2-2) comprising the polyether polyol (B2-1) as an essential constitutional unit, polyester polyols that can be induced from the polyether polyols (B2-1), and a dicarboxylic acid, an anhydride of a dicarboxylic acid, or a lower alkyl ester of a dicarboxylic acid, and the like can be used.

Suitable examples of the polyester polyols (B2-2) include polyester polyols that can be induced from polypropylene glycol (an adduct of 1,2- or 1,3-propylene oxide to propylene glycol), adducts of ethylene oxide to polyalkylene glycols (such as a block adduct of ethylene oxide and propylene oxide to ethylene glycol or propylene glycol, in which the content of ethylene oxides is 5 to 45% by weight), random copolymers of propylene oxide and ethylene oxide (such as a random adduct of ethylene oxide and propylene oxide to ethylene glycol or propylene glycol, in which the content of ethylene oxides is 10 to 25% by weight), polytetramethylene glycol (an adduct of 1,2-, 1,3-, 2,3-, or 1,4-butylene oxide to 1,4-butylene glycol), and/or copolymers of 1,4-butylene oxide and ethylene oxide (such as a block or random adduct of 10 to 25% by weight of ethylene oxide and 75 to 95% by weight of 1,4-butylene oxide to ethylene glycol or butylenes glycol, in which the content of ethylene oxides is 10 to 25% by weight), and dicarboxylic acids (such as adipic acid, sebacic acid, maleic acid, and phthalic acid), anhydrides of the dicarboxylic acid and/or lower alkyl esters of the dicarboxylic acid (such as methyl ester and ethyl ester of the dicarboxylic acid); and the like.

These polyester polyols (B2-2) may be one kind or a mixture of two kinds or more.

The equivalent weight of the hydroxyl group in the polyester polyol (B2-2) is the same as that of the polyester polyol (B1-2).

As the polyester polyol (B2-3) not containing an oxyethylene group and an oxyalkylene group having 3 to 8 carbon atoms, polyesters that can be induced from diols and/or polyols of 3 to 6 in valence and the above-mentioned dicarboxylic acid, an anhydride of the dicarboxylic acid and/or a lower alkyl ester of the dicarboxylic acid, polyesters induced by the ring-opening polymerization of caprolactone, and the like can be used.

Suitable examples of the polyester polyols (B2-3) include polyester diols induced from butanediols and adipic acid; polyester diols induced from ethylene glycol and adipic acid; polyester diols induced from hexamethylene glycol and adipic acid; polyester diols induced from ethylene glycol, butanediols and adipic acid; polyester diols induced from ethylene glycol and sebacic acid; polyester diols induced from cyclohexanediol and phthalic acid; polycaprolactones induced by the ring-opening polymerization of caprolactone; and the like.

These polyester polyols (B2-3) may be one kind or a mixture of two kinds or more.

The number average molecular weight per one hydroxyl group (the equivalent weight of the hydroxyl group) in the polyester polyol (B2-3) is the same as that of the polyester polyol (B1-2).

Among these low-hydrophilic other polyols (B2), the polyether polyols (B2-1) wherein the content of oxyethylene groups is less then 30% by weight are preferable, polypropylene glycol and adducts of 5 to 15% by weight ethylene oxide to polypropylene glycol are more preferable, and polypropylene glycol are particularly preferable, from the adhesive strength and the like viewpoints.

The equivalent weight of the hydroxyl group in these low-hydrophilic other polyols (B2) is preferably from 50 to 5,000, more preferably from 100 to 3,000, and particularly preferably from 200 to 2,000. Within this range, the adhesive strength and the like become further excellent.

When the low-hydrophilic other polyol (B2) is used, the content (% by weight) of hydrophilic polyols (B1) is preferably from 30 to 99, more preferably from 50 to 98, and particularly preferably from 80 to 95, based on the weight of the polyol components (B). Within this range, the adhesive strength and the like become further excellent.

When the low-hydrophilic polyol (B2) is used, the content (% by weight) of the polyols (B2) is preferably from 1 to 70, more preferably from 2 to 50 and particularly preferably from 5 to 20, based on the weight of the polyol components (B).

Moreover, in this case, the content (% by weight) of oxyethylene groups in the whole polyol components (B) is preferably from 30 to 100, more preferably from 35 to 98, particularly preferably from 40 to 95, and most preferably from 50 to 90, based on the weight of the oxyalkylene groups in (B). Within this range, the adhesive strength and the like become further excellent.

Moreover, the average equivalent weight of the hydroxyl group in the whole polyol components (B) is preferably from 50 to 5,000, more preferably from 100 to 4,000, and particularly preferably from 200 to 3,000. Within this range, the adhesive strength and the like become further excellent.

When the low-hydrophilic other polyol (B2) is used in combination, as the hydrophilic polyol (B1), adducts of ethylene oxide to diols (such as an adduct of ethylene oxide to ethylene glycol and an adduct of ethylene oxide to propylene glycol), co-adducts of ethylene oxide and an alkylene oxide having 3 to 8 carbon atoms to diols (such as a random or block co-adduct of ethylene oxide and propylene oxide to ethylene glycol and a random or block co-adduct of ethylene oxide and butylene oxide to ethylene glycol) and the like are preferable, co-adducts of ethylene oxide and propylene oxide to diols are more preferable, and random co-adducts of ethylene oxide and propylene oxide to diols are particularly preferable.

In this case, as the low-hydrophilic other polyol (B2), besides diols and polyols of 3 to 6 in valence, polyether polyols wherein the content of oxyethylene groups is less than 30% by weight based on the weight of oxyalkylene groups are preferable, polyether polyols that contain an oxypropylene group and wherein the content of oxyethylene groups is less than 30% by weight based on the total weight of the oxyethylene groups and the oxypropylene groups are more preferable, and polypropylene glycol is particularly preferable.

The content (mmol/kg) of alkaline metals and alkaline earth metals in the polyol component (B) is preferably from 0 or less than 0.07, more preferably from 0 or less than 0.04, particularly preferably from 0 or less than 0.02, and most preferably from 0 or less than 0.01, based on the weight of (B). Within this range, it is easy to prevent an abnormal reaction from occurring during the reaction of the fluorine-containing nonaromatic polyisocyanate component (A) and the polyol component (B).

Further, the content of alkaline metals and alkaline earth metals in the polyol component (B) can be determined by some methods: the method in which a 30% by weight methanol solution of (B) or an aqueous ashed (B) solution, prepared in such a way that 10 g of (B) is incinerated on a platinum dish and the ash is dissolved in 10 g of water, is analyzed by ion chromatography, the method in which 30 g of (B) is dissolved in 100 ml of methanol and the solution is then titrated with aqueous hydrochloric acid solution of $1/100$ N, and the like methods.

Alkaline metals and alkaline earth metals are mainly used as a catalyst in polyether polyol synthesis. Such catalysts include hydroxides (such as potassium hydroxide, sodium hydroxide, cesium hydroxide, beryllium hydroxide, and magnesium hydroxide), alcoholates (such as lithium methylate, sodium ethylate, potassium butylate, and magnesium hexylate), simple metals (such as potassium, sodium, lithium, magnesium, and calcium), and the like. These catalysts often remain at a rate of 0.1 to 0.3 mmol/kg in (B). In order to make the content of alkaline metals and alkaline earth metals in (B) keep within the above-mentioned range, a polyether polyol and the like with low content of alkaline metals and alkaline earth metals have only to be used.

The polyether polyol with low content of alkaline metals and alkaline earth metals can be obtained by the following methods: the method in which after a crude polyether polyol is obtained by the addition polymerization of alkylene oxide to a compound having an active hydrogen in the presence of the catalyst as mentioned above, alkaline metals and alkaline earth metals are removed, the method in which an addition polymerization of alkylene oxide is performed in the presence of a catalyst having no alkaline metal and alkaline earth metal such as composite metal cyamide complexes (such as the complex catalyst of zinc hexacyanocobaltate and polyether) disclosed in Japanese Kokai Publication Hei-8-104741 (corresponding patent application: U.S. Pat. No. 5,482,908A, U.S. Pat. No. 5,536,883A, and the like), organic boron compounds (such as trifluoroboron and tris(pentafluorophenyl) borane), and transition metal complex catalysts, and the like methods. Methods of removing alkaline metals and alkaline earth metals from a crude polyether polyol include a method comprising a treatment with an adsorbent, a method comprising a treatment with an ion-exchanging agent, and the like methods.

Adsorbents include silicates (such as magnesium silicate, talc, soapstone, stealite, calcium silicate, magnesium aluminosilicate, and sodium aluminosilicate), clay (such as activated clay and acid clay), hydrotarsite, silica gel, diatomite, activated alumina and the like. Among these adsorbents, silicates are preferable and magnesium silicate is more preferable.

The ion-exchanging agents include strong cation-exchange resin, weak cation-exchange resin, chelate resin and the like. The methods comprising a treatment with an ion-exchanging agent include a method in which water is added to a crude polyether polyol, the mixture is then mixed and stirred with an ion-exchanging agent followed by removal of the ion-exchanging agent by filtration, a method in which the above-mentioned mixture is passed through a column filled with an ion-exchanging agent, and the like methods.

The filtration devices such as filter paper, filter cloth, and glass filters are used for the filtration.

The hydrophilic urethane prepolymer (UP) can be obtained by reacting (by a prepolymer reaction) the fluorine-containing nonaromatic polyisocyanate component (A) with the polyol component (B) comprising the hydrophilic polyol component (B1) as an essential component.

The ratio of the amount of the polyisocyanate component (A) and the polyol component (B) is preferably such that the equivalent weight ratio of isocyanate groups in (A) and hydroxyl groups in (B) (NCO group/OH group) is 1.5 to 3, more preferable 1.8 to 2.3, and particularly preferable 1.9 to 2.1. Within this range, the viscosity is relatively low and the urethane polymer becomes further easy to be handled as an adhesive, and the adhesive strength becomes excellent further, too.

It is preferable that the hydrophilic urethane prepolymer (UP) has at least one (preferably two) isocyanate group within the molecule, and has a structure without an active hydrogen.

Further, the position of the isocyanate group in the hydrophilic urethane prepolymer (UP) is preferably the position where the steric hindrance is small and more preferably the terminal position where the steric hindrance is small, from the reactivity with blood and body fluid etc., and the like viewpoints.

Moreover, the content (% by weight) of isocyanate groups in a medical adhesive (the weight ratio of isocyanate groups occupied in the total weight of the medical adhesive) is preferably from 1 to 10, more preferably from 1.2 to 8, and particularly preferably from 1.5 to 6. Within this range, the adhesive strength becomes further excellent.

The content of isocyanate groups can be measured in such a method that the excessive amount of di-n-butylamine solution is added to and reacted with the sample, and then unreacted di-n-butylamine is back-titrated with hydrochloric acid standard solution, for example, measured according to JIS K7301-1995, "6.3 the content of isocyanate groups."

The content (% by weight) of oxyethylene groups in the hydrophilic urethane prepolymer (UP) is preferably from 30 to 100, more preferably from 50 to 98, particularly preferably from 60 to 95, and most preferably from 70 to 90, based on the weight of the oxyalkylene groups in (UP). Within this range, the adhesive strength (particularly the initial adhesive strength) becomes further excellent.

The number average molecular weight (Mn) of the hydrophilic urethane prepolymer (UP) is preferably from 500 to 30,000, more preferable 800 to 20,000, particularly preferably from 1,000 to 10,000, and most preferably from 1,200 to 8,000. Within this range, the adhesive strength becomes further excellent.

Further, the number average molecular weight (Mn) is measured by gel permeation chromatography (GPC) using polyoxyethylene glycol as a standard substance.

As the method of producing this hydrophilic urethane prepolymer (UP), there may be mentioned a well-known method (such as the method in International publication WO03/051952 (the disclosure of U.S. patent application Ser. No. 10/499,331 is incorporated herein by reference)), and for example a method in which the fluorine-containing nonaromatic polyisocyanate component (A) and the polyol component (B) are reacted at 50 to 100° C. for 1 to 10 hours, and the like methods can be cited. In this case, as a method of pouring the fluorine-containing nonaromatic polyisocyanate component (A) and the polyol component (B), a method in which they are added from the beginning and a method in which they are dropped gradually may be used.

Because the fluorine-containing nonaromatic polyisocyanate (A) is extremely easy to react with moisture, it is necessary to remove water in the reaction device and the raw materials as much as possible. Especially, it is preferable to dehydrate the polyol component (B) that contains water easily. As the dehydration treatment, for example, such a method can be applied that the dehydration is carried out at temperatures of 50 to 150° C., and under pressures of 0.001 hPa to atmospheric pressure for 0.5 to 10 hours while aerating the inert gas (such as nitrogen gas) if necessary.

As a method of mixing the fluorine-containing nonaromatic polyisocyanate component (A) and the polyol component (B), any of the following method may be used: (1) the method of mixing them at a time, (2) the method of gradually dropping (B) into (A), (3) the method of gradually dropping (A) into (B), (4) the method in which (A) and part of (B) are mixed and reacted previously, and the remaining (B) is then dropped into this mixture or mixed with this mixture at a time, and the like methods. Among these methods, the method of (1) and the method of (2) are preferable and the method of (1) is more preferable because of simplicity of the reaction operation and the like.

The reaction may be carried out in the presence of a catalyst (including organometallic compounds such as dibutyltin oxide and dibutyltin dilaurate, organic metal salts such as zirconium acetate, and the like).

The medical adhesive of the present invention contains further a phenolic radical scavenger (PRS). When (PRS) is contained, the deterioration and decomposition, with the passage of time, of a sheet-like or sponge-like product cured by the reaction with water produced by the reaction of the hydrophilic urethane prepolymer (UP) with water is controlled, and the decrease in adhesiveness can be prevented.

As the phenolic radical scavenger (PRS), mono-phenolic, bisphenolic and polymer-type phenolic radical scavengers, and the like are included.

The mono-phenolic radical scavengers include 2,6-di-t-butyl-p-cresol (for example, Antage BHT, manufactured by Kawaguchi Chemical Industry Co., Ltd.), butylated hydroxyanisole (for example, Orient BHT, manufactured by Orient Chemical Industries, Ltd.), 2,6-di-t-butyl-4-ethylphenol (for example, NOCTIZER M-17, manufactured by Ouchi Shinko Chemical Industrial Co., Ltd.), stearyl-$\beta$-(3,5-di-t-butyl-4-hydroxyphenyl)propionate (for example, Adekastab AO-50, manufactured by Asahi Denka Co., Ltd.), and the like.

The bisphenolic radical scavengers include 2,2'-methylenebis(4-methyl-6-t-butylphenol) (for example, Antage W-400, manufactured by Kawaguchi Chemical Industry Co., Ltd.), 2,2'-methylenebis(4-ethyl-6-t-butylphenol) (for example, Antage W-500, manufactured by Kawaguchi Chemical Industry Co., Ltd.), 4,4'-butylidenebis(3-methyl-6-t-butylphenol) (for example, Antage Crystal, manufactured by Kawaguchi Chemical Industry Co., Ltd.), 4,4'-thiobis(3-methyl-6-t-butylphenol) (for example, Antage W-300, manufactured by Kawaguchi Chemical Industry Co., Ltd.), 1,6-hexanediol-bis[3-(3,5-di-t-butyl-4-hydroxyphenyl)

propionate] (for example, IRGANOX s259, manufactured by Ciba Speciality Chemicals), 3,9-bis[1,1-dimethyl-2-[(β-(3-t-butyl-4-hydroxy-5-methylphenyl)propionyl]ethyl]2,4,8,10-tetraoxaspiro[[5,5]]undecane (for example, Adekastab AO-80, manufactured by Asahi Denka Co., Ltd.), and the like.

The polymer-type phenolic radical scavengers include tetrakis-[methylene-3-(3',5'-di-t-butyl-4'-hydroxyphenyl)propionate]methane (for example, IRGANOX 1010, manufactured by Ciba Speciality Chemicals), 1,3,5-trimethyl-2,4,6-tris(3,5-di-t-butyl-4-hydroxybenzyl)benzene (for example, Adekastab AO-330, manufactured by Asahi Denka Co., Ltd.), 1,1,3-tris(2-methyl-4-hydroxy-5-t-butylphenyl)butane (for example, Adekastab AO-30, manufactured by Asahi Denka Co., Ltd.), bis[3,3'-bis-(4'-hydroxy-3'-t-butylphenyl)butylic acid]glycol ester (for example, Antioxidant TMOZ, manufactured by Hoechst AG), 1,3,5-tris(3',5'-di-t-butyl-4'-hydroxybenzyl)-sec-triazine-2,4,6-(1H, 3H, 5H)trion (for example, Adekastab AO-20, manufactured by Asahi Denka Co., Ltd.), and the like.

The molecular weight of the phenolic radical scavenger (PRS) is preferably 500 to 1,200, more preferably 600 to 1,100, and particularly preferably 700 to 1,000. Within this range, the product cured by the reaction with water becomes further not be easily deteriorated and decomposed with the passage of time. That is, the duration of adhesive strength becomes further excellent.

The phenolic radical scavenger (PRS) is preferable to have at least two hydroxyl groups, more preferably two to five hydroxyl groups, and particularly preferably three to four hydroxyl groups. Within this range, the product cured by the reaction with water becomes further not be easily deteriorated and decomposed with the passage of time. That is, the duration of adhesive strength becomes further excellent.

Among these phenolic radical scavengers, bisphenolic radical scavengers and polymer-type phenolic radical scavengers are preferable, and tetrakis-[methylene-3-(3',5'-di-t-butyl-4'-hydroxyphenyl)propionate]methane, 1,1,3-tris(2-methyl-4-hydroxy-5-t-butylphenyl)butane, 1,3,5-trimethyl-2,4,6-tris(3,5-di-t-butyl-4-hydroxybenzyl) benzene, 1,3,5-tris(3',5'-di-t-butyl-4'-hydroxybenzyl)-sec-triazine-2,4,6-(1H, 3H, 5H)trion, and 1,6-hexanediol-bis[3-(3,5-di-t-butyl-4-hydroxyphenyl)propionate] are more preferable, from the viewpoint of controlling the deterioration and decomposition of the product cured by the reaction with water with the passage of time, and the like.

Further, even in the same radical scavengers, as for radical scavengers other than phenolic radical scavengers, for example, aromatic amine radical scavengers (such as octylated diphenylamine, N-n-butyl-p-aminophenol, and phenothiazine), sulfuric radical scavengers (such as dilauryl-3, 3'-thiodipropionate, distearyl-3,3'-thiodipropionate, and pentaerythritol tetrakis(3-laurylthiopropionate)), and phosphorous radical scavengers (such as trisnonylphenyl phosphite, tris(2,4-di-t-butylphenyl)phosphite, and distearyl pentaerythritol diphosphite), the effects like the medical adhesive of the present invention (that is, the product cured by the reaction with water are not easily deteriorated and decomposed with the passage of time, and the adhesive is excellent in the duration of adhesive strength) is not observed (see Comparative examples 3 and 4). That is, only the phenolic radical scavenger (PRS) can control the deterioration and decomposition of the product cured by the reaction with water of the hydrophilic urethane prepolymer (UP) with the passage of time, and can exhibit excellent duration of adhesive strength. Further, if a radical scavenger contains a phenolic radical scavenger (PRS), the radical scavenger may contain a radical scavenger other than (PRS).

The content (% by weight) of these phenolic radical scavengers (PRS) is preferably from 0.01 to 3, more preferably from 0.02 to 1, and particularly preferably from 0.05 to 0.5, based on the weight of the hydrophilic urethane prepolymer (UP). Within this range, the deterioration and decomposition of the product cured by the reaction with water with the passage of time can be prevented, and there is no adverse effect.

The phenolic radical scavenger (PRS) may be added to the hydrophilic urethane prepolymer (UP), or the hydrophilic urethane prepolymer (UP) may be obtained after adding the scavenger (PRS) to the fluorine-containing nonaromatic polyisocyanate (A) and/or the polyol component (B) in advance.

The medical adhesive of the present invention can contain other components than the hydrophilic urethane prepolymer (UP) and the phenolic radical scavenger (PRS) according to need.

Other components include bioactive drugs (such as drugs for the central nervous system, drugs for allergy, circulatory drugs, respiratory drugs, drugs for digestive organs, hormone drugs, metabolic drugs, anticancer drugs, antibiotics, and chemotherapeutic drugs), fillers (such as carbon black, colcothar, calcium silicate, sodium silicate, titanium oxide, acrylic resin powders, and various ceramic powders), plasticizers (such as DBP, DOP, TCP, tributoxyethylphosphate, and other various esters), and the like. When other components are contained, these contents are properly decided according to the use and the like. Other components may be mixed with the fluorine-containing nonaromatic polyisocyanate component (A), the polyol component (B) and/or the phenolic radical scavenger (PRS) in advance for prepolymer reaction, or may be added to the hydrophilic urethane prepolymer (UP) and/or the phenolic radical scavenger (PRS) after the reaction of these.

The viscosity (at 37° C.) of the medical adhesive of the present invention is preferably 0.5 to 500 Pa·s, more preferably 1 to 200 Pa·s, particularly preferably 3 to 100 Pa·s, and most preferably 5 to 50 Pa·s. Within this range, the coating property of the adhesive becomes excellent further.

Viscosity is measured according to JIS K7117-2: 1999"viscosity measuring method for plastics (liquid, emulsion-like or dispersed resin) by a rotational viscometer at a fixed shearing speed" with the use of a rotational viscometer (for example, EL type viscometer and EH type viscometer, manufactured by Tokimec, Inc.).

The maximum amount of water absorption of the medical adhesive of the present invention is preferably 0.2 to 5 ml/g, more preferably 0.3 to 3 ml/g, particularly preferably 0.4 to 1 ml/g, and most preferably 0.5 to 0.7 ml/g. Within this range, the adhesive strength (especially, the initial adhesive strength) becomes high further.

The maximum amount of water absorption is measured with the use of the measuring device of rate of water absorption in D/W method (see FIG. 1; buret (2) of 25 ml in capacity, 55 cm in length, and 2 mm in diameter of small hole) described in Explanatory FIG. 1 in JIS K7224-1996 "Testing method of rate of water absorption in high-water absorption resin," in which device a filter paper of 3.7 cm in diameter {(5), glass microfiber filter paper GF/A, manufactured by Whatman plc, and the like} is set up in place of nonwoven fabric in a room of 25° C. and 50% in humidity. First, after 25 ml of a testing liquid {(3) physiological saline} is poured into the buret with valves (7) and (8) shut, the space between valves (7) and (8) is filled with the testing liquid from the buret (2) by opening valves (7) and (8). Next, after the rubber stopper (1) is installed, the valve (7) under the buret is opened and the testing liquid that begins to overflow from the filter paper (5) is wiped off, and the graduation (a1) of the buret is read. Then, 1.0 g of the measurement sample (4) is flowed and spread onto the filter paper (5) and the graduation (a2) of the buret is read 30 minutes later, and the value that (a1) is subtracted from (a2) is assumed to be the maximum amount of water absorption.

The initial rate of water absorption of the medical adhesive of the present invention is preferably 0.01 to 0.5 ml/g·min, more preferably 0.02 to 0.3 ml/g·min, particularly preferably 0.03 to 0.2 ml/g·min, and most preferably 0.04 to 0.1 ml/g·min. Within this range, the adhesive strength (especially, the initial adhesive strength) becomes high further.

As for the initial rate of water absorption, with the same method and the same device as those for the maximum amount of water absorption measurement, the measurement sample is placed onto the filter paper (5) and the graduation (a3) of the buret is read two minutes later, and ½ of the value that (a1) is subtracted from (a3) is assumed to be the initial rate of water absorption (ml/g·min).

The content (mmol/kg) of alkaline metals and alkaline earth metals in the medical adhesive of the present invention is preferably from 0 or less than 0.04, more preferably from 0 or less than 0.03, particularly preferably from 0 or less than 0.02, and most preferably from 0 or less than 0.01, based on the weight of the hydrophilic urethane prepolymer (UP). Within this range, the stability with time of the medical adhesive of the present invention becomes further high.

Further, the content of alkaline metals and alkaline earth metals can be determined by the following methods: a method in which 30% by weight of medical adhesive solution in a solvent such as toluene, dimethylformamide or dimethyl sulfoxide, or a pretreated sample such that 10 g of the medical adhesive is incinerated on a platinum dish and the ash is dissolved in 10 g of water is analyzed by ion chromatography, a method in which 30 g of the medical adhesive is dissolved in 100 ml of a solvent such as toluene, dimethylformamide or dimethyl sulfoxide, and the solution is titrated with aqueous hydrochloric acid solution of $\frac{1}{100}$ N, and the like methods.

As for the cured coat obtained by reacting the medical adhesive of the present invention with water, the wet 100% modulus is preferably 0.01 to 1.0 MPa, more preferably 0.05 to 5 MPa, particularly preferably 0.1 to 2 MPa, and most preferably 0.4 to 0.7 MPa. Within this range, the adhesive strength (especially water-resistant adhesive strength) becomes further high.

The wet 100% modulus is measured as follows.

A medical adhesive is applied onto a glass plate in the thickness of about 100 μm and the size with all sides of 10 cm with an applicator, and left alone for 48 hours under the conditions of 25° C. and 50% RH for curing slowly, and then the coated glass plate is left in a physiological saline bath of one liter at 25° C. for 24 hours in order to give a cured coat. Then, a No. 3 type dumbbell form sample defined in JIS K6251: 2004 (corresponding International Standard ISO 37: 1994) is punched out from the cured coat.

Next, after this punched sample is soaked in physiological saline of 25° C. for one hour, water is removed from the sample with gauze and the thickness thereof is measured accurately. And then, within 5 minutes, the tensile stress of the sample at 100% elongation is measured at pulling speed of 300 mm/min under the environment of 25° C. and 50% RH according to JIS K6251: 2004. As a tensile testing machine, a testing machine according to JIS K6272: 2003 (corresponding International Standard ISO 5893: 2002) (for example, Autograph AGS-500B, manufactured by Shimadzu Corporation) and the like can be used.

As for the cured coat obtained by reacting the medical adhesive of the present invention with water, the wet elongation percentage is preferably 100 to 1,500%, more preferably 200 to 1,200, particularly preferably 300 to 1,000, and most preferably 400 to 800. Within this range, the adhesive strength (especially water-resistant adhesive strength) becomes further high.

As for the wet elongation percentage, after a punched sample made in the same method as for the wet 100% modulus measurement is soaked in physiological saline of 25° C. for one hour, water is removed from the sample with gauze and the thickness thereof is measured accurately. And then, within 5 minutes, elongation at break is measured at pulling speed of 300 mm/min under the environment of 25° C. and 50% RH according to JIS K6251: 2004.

The adhesive of the present invention can be produced by the methods: method (1) the fluorine-containing nonaromatic polyisocyanate (A) and/or the polyol component (B), and the phenolic radical scavenger (PRS) and, according to need, other components are mixed together and then (A) and (B) are reacted, method (2) the hydrophilic urethane prepolymer (UP) and (PRS), and, according to need, other components are mixed together, and the like methods. As a mixing method, there are no limitation for the condition and the device if uniform dissolution or uniform dispersion can be done. However, because the hydrophilic urethane prepolymer (UP) has the tendency to cause polymerization easily by water, it is necessary not to contain water in the phenolic radical scavenger (PRS) and other components. The mixing is preferably carried out in the dry gas atmosphere {though an inert gas (such as nitrogen gas and argon gas) and air etc. can be used, the inert gas is preferable} so that the mixture should not come in contact with moisture. The mixing temperature is preferably from 0 to 60° C., more preferably from 5 to 40° C., and particularly preferably from 10 to 30° C.

The adhesive of the present invention is preferably from preserved so as not to come in contact with moisture etc. (for example, it is preferably from filled in an ampule container or a syringe which intercepts air) from the reaction with moisture, and the like viewpoints.

When the medical adhesive of the present invention is used, the hydrophilic urethane prepolymer (UP) reacts with water (including, for example, water in the body fluid such as blood and lymph) to form an amine and carbon dioxide, and this amine further reacts with (UP) and promotes molecular weight-increasing process (polymerization). At this time, a foam-like (sponge-like) product cured by the reaction with water is formed by the generated carbon dioxide.

Therefore, when being applied to the medical practice such as operations, and the like, the medical adhesive of the present invention comes in contact with the body fluid including blood and the polymerization progresses rapidly, resulting in bonding the applied site. The initial adhesiveness and the hemostatic effect and the like can be improved by supplying more water through, for example, the atomization of physiological saline and the like if necessary.

In operations, application methods for suturing the body tissues with the adhesive of the present invention include the direct application method in which the adhesive of the present invention is directly applied on the incised part; the transcription application method in which the adhesive is applied on a film with high removability such as a silicone film and then the incised part is covered with the film, and the film is removed after the reaction; and the like methods.

The medical adhesive of the present invention is suitable for bonding or sealing of body tissues such as internal organs, skins, and mucous membranes, further suitable for solid organs such as lung, heart, trachea, esophagus, stomach, duodenum, small intestine, colon, rectum, liver, spleen, kidney, and pancreas, blood vessel such as artery, vein, and capillary, lymphatic vessel, and nerve, still further suitable for heart, blood vessel such as artery, respiratory organ, and digestive organ, and particularly suitable for blood vessel. The medical adhesive can be applied not only to the body tissues but also to artificial materials such as vascular prostheses. Moreover, as for the body tissue, tissues of animals (such as pets and domestic animals) other than mankind are included.

Further, the medical adhesive of the present invention shows an especially remarkable effect as a hemostatic sealant in the bleeding part. Especially, in a surgical operation of artery blood vessel and heart, it is also possible to stop spurting bleeding in a short period of time by applying the hemostatic sealant which comprises the medical adhesive of the present invention to the bleeding part.

As for an application method of the hemostatic sealant, any of the direct application method and the transcription application method can be used.

For example, in a surgical operation of heart and aorta that uses an artificial heart-lung machine, an anticoagulant such as a heparin is administered without fail. Because the bleeding blood does not coagulate while this anticoagulant acts, a large amount of bleeding under the operation might become a fatal trouble for the patient. However, even in such a case, with the hemostatic sealant comprising the medical adhesive of the present invention, it is possible to stop bleeding in a short period of time regardless of the presence of the administration of an anticoagulant.

Next, methods of applying the hemostatic sealant of the present invention for the bleeding from the space between suture threads at an anastomosis site of a blood vessel and a blood vessel, or at an anastomosis site of a blood vessel and an vascular prosthesis will be illustrated.

The hemostatic sealant of the present invention is applied on the bleeding part while forcipes nip both ends of the anastomosis site and the bleeding is being suppressed and, after waiting for the curing of the sealant by the water in blood, and the like (for 2 to 5 minutes), the forcipes are removed. If necessary, more water is supplied by atomizing physiological saline to the sealant under curing.

EFFECT OF THE INVENTION

The medical adhesive of the present invention is extremely excellent in the duration of adhesive strength because the cured product obtained from the curing of the adhesive is difficult to deteriorate and decompose (adhesive strength is difficult to decrease) with the passage of time. Further, the safety of the medical adhesive of the present invention is high because the adhesive does not contain any aromatic polyisocyanate that has some problems in mutagenicity and the like, and the adhesive can react immediately with water in the body fluid (such as blood) to be cured and bonded because of containing a fluorine-containing polyisocyanate.

BRIEF DESCRIPTION OF THE DRAWING

FIG. 1 is an elevation cross-sectional view schematically showing the measuring device of rate of water absorption in D/W method to measure the maximum amount of water absorption (ml/g) of the medical adhesive of the present invention (quoted from Explanatory FIG. 1 in JIS K7224-1996 "Testing method of rate of water absorption in high-water absorption resin.")

DESCRIPTION OF REFERENCE NUMERALS

| | |
|---|---|
| 1. | Rubber Stopper |
| 2. | Buret |
| 3. | Testing Liquid |
| 4. | Measurement Sample |
| 5. | Filter Paper |
| 6. | Supporting Plate Having Open Small Holes (Diameter: 2 mm) |
| 7. | Valve |
| 8. | Valve |

BEST MODE FOR CARRYING OUT THE INVENTION

Hereinafter, although the present invention will be explained in more detail by showing examples, the present invention should not be limited only to these examples. Further, "part" represents "part by weight" and "%" represents "% by weight".

Production Example 1

After 15.5 parts of ethylene glycol and 3.8 parts of potassium hydroxide were fed into an autoclave and substituted with nitrogen (the oxygen concentration in the vapor phase was 450 ppm), the inside of the autoclave was vacuum dehydrated at 120° C. for 60 minutes.

Then, after the mixture of 784.5 parts of ethylene oxide and 200 parts of propylene oxide was fed at temperatures of 100 to 130° C. for about 10 hours, the reaction was continued at 130° C. for 3 hours, and liquid crude polyether in which the content of oxyethylene groups was 80% was obtained.

One thousand parts of this liquid crude polyester was put in an autoclave followed by substitution with nitrogen (the oxygen concentration in the vapor phase was 450 ppm), and then 30 parts of ion-exchanged water was added. After that, 10 parts of synthetic magnesium silicate (sodium content of 0.2%) was added followed by substitution with nitrogen again, and then the mixture was stirred with the stirring speed of 300 rpm at 90° C. for 45 minutes. Next, using a glass filter (GF-75, manufactured by Toyo Roshi Kaisha, Ltd.), the mixture was filtered under nitrogen and a random co-adduct of ethylene oxide/propylene oxide (b1) was obtained. As for this (b1), the number average molecular weight was 4,000, the content of oxyethylene groups was 80%, and the content of alkaline metals and/or alkaline earth metals was 0.02 mmol/kg.

Production Example 2

After 15.5 parts of ethylene glycol and 3.8 parts of potassium hydroxide were fed into an autoclave followed by substitution with nitrogen (the oxygen concentration in the vapor phase was 450 ppm), the inside of the autoclave was vacuum dehydrated at 120° C. for 60 minutes.

Then, after the mixture of 209 parts of ethylene oxide and 116 parts of propylene oxide was fed at temperatures of 100 to 130° C. for about 10 hours, the reaction was continued at 130° C. for 3 hours, and liquid crude polyether in which the content of oxyethylene groups was about 60% was obtained.

This liquid crude polyether was treated with the synthetic magnesium silicate in the same method as that of the above-mentioned Production Example 1 and a random co-adduct of ethylene oxide/propylene oxide (b2) was obtained. As for this (b2), the number average molecular weight was 1,400, the content of oxyethylene groups was 60%, and the content of alkaline metals and/or alkaline earth metals was 0.04 mmol/kg.

Production Example 3

After 362 parts of propylene glycol and 3.8 parts of potassium hydroxide were fed into an autoclave followed by substitution with nitrogen (the oxygen concentration in the vapor phase was 450 ppm), the inside of the autoclave was vacuum dehydrated at 120° C. for 60 minutes.

Then, after 632 parts of propylene oxide was fed at temperatures of 100 to 130° C. for about 10 hours, the reaction was continued at 130° C. until the content of volatile matters became 0.1% or less in order to obtain a liquid crude polyether.

This liquid crude polyether was treated with the synthetic magnesium silicate in the same method as that of the above-mentioned Production Example 1 and an adduct of propylene oxide (b3) was obtained. As for this (b3), the number average molecular weight was 210, the content of oxyethylene groups was 0%, and the content of alkaline metals and/or alkaline earth metals was 0.04 mmol/kg.

Production Example 4

After 180 parts of propylene glycol and 3.8 parts of potassium hydroxide were fed into an autoclave followed by substitution with nitrogen (the oxygen concentration in the vapor phase was 450 ppm), the inside of the autoclave was vacuum dehydrated at 120° C. for 60 minutes.

Then, after 820 parts of propylene oxide was fed at temperatures of 100 to 130° C. for about 10 hours, the reaction was continued at 130° C. until the content of volatile matters became 0.1% or less in order to obtain a liquid crude polyether.

This liquid crude polyether was treated with the synthetic magnesium silicate in the same method as that of the above-mentioned Production Example 1 and an adduct of propylene oxide (b4) was obtained. As for this (b4), the number average molecular weight was 420, the content of oxyethylene groups was 0%, and the content of alkaline metals and/or alkaline earth metals was 0.03 mmol/kg.

Production Example 5

After 80 parts of propylene glycol and 3.8 parts of potassium hydroxide were fed into an autoclave followed by substitution with nitrogen (the oxygen concentration in the vapor phase was 450 ppm), the inside of the autoclave was vacuum dehydrated at 120° C. for 60 minutes.

Then, after 920 parts of propylene oxide was fed at temperatures of 100 to 130° C. for about 10 hours, the reaction was continued at 130° C. until the content of volatile matters became 0.1% or less in order to obtain a liquid crude polyether.

This liquid crude polyether was treated with the synthetic magnesium silicate in the same method as that of the above-mentioned Production Example 1 and an adduct of propylene oxide (b5) was obtained. As for this (b5), the number average molecular weight was 950, the content of oxyethylene groups was 0%, and the content of alkaline metals and/or alkaline earth metals was 0.03 mmol/kg.

Production Example 6

After 244 parts of adduct of propylene oxide (b5) produced in Production Example 5 and 1.8 parts of potassium hydroxide were fed into an autoclave followed by substitution with nitrogen (the oxygen concentration in the vapor phase was 450 ppm), the inside of the autoclave was vacuum dehydrated at 120° C. for 30 minutes.

Then, after 756 parts of propylene oxide was fed at temperatures of 100 to 130° C. for about 10 hours, the reaction was continued at 130° C. until the content of volatile matters became 0.1% or less in order to obtain a liquid crude polyether.

This liquid crude polyether was treated with the synthetic magnesium silicate in the same method as that of the above-mentioned Production Example 1 and an adduct of propylene oxide (b6) was obtained. As for this (b6), the number average molecular weight was 3,900, the content of oxyethylene groups was 0%, and the content of alkaline metals and/or alkaline earth metals was 0.01 mmol/kg.

Example 1

100 parts of the random co-adduct of ethylene oxide/propylene oxide (b1) obtained in Production Example 1, as the polyol component (B), was dehydrated under reduced pressure and nitrogen atmosphere at 100° C. for 2 hours, followed by cooling to 50° C. Then, 0.5 parts of tetrakis-[methylene-3-(3',5'-di-t-butyl-4'-hydroxyphenyl) propionate]methane (IRGANOX 1010, manufactured by Ciba Speciality Chemicals) was added thereto as the phenolic radical scavenger (PRS) and the mixture was stirred uniformly for 30 minutes. After the mixture was cooled to 40° C., 15.6 parts of bis(isocyanatomethyl)perfluorobutane [OCN—$CH_2$—$(CF_2)_4$—$CH_2$—NCO] (the ratio of NCO group/OH group=2/1) was added as the fluorine-containing nonaromatic polyisocyanate component (A), the resultant mixture was stirred uniformly and then heated to 80° C. followed by a reaction at 80° C. for 6 hours in order to obtain the medical adhesive (P1) of the present invention. As for this (P1), the content of isocyanate groups was 1.8%, the number average molecular weight (Mn) was 5,800, and the content of alkaline metals and/or alkaline earth metals was 0.03 mmol/kg. The content of the oxyethylene groups in the polyol component (B) was 80% by weight, and the content of oxyethylene groups in (UP) was 69% by weight.

Example 2

The medical adhesive (P2) of the present invention was obtained by the same method as that in Example 1, except using 100 parts of the random co-adduct of ethylene oxide/propylene oxide (b2) obtained in Production Example 2 as the polyol component (B) and 46.6 parts of bis(isocyanatomethyl)perfluorohexane [OCN—$CH_2$—$(CF_2)_6$—$CH_2$—NCO] (the ratio of NCO group/OH group=2/1) as the fluorine-containing nonaromatic polyisocyanate component (A). As for this (P2), the content of isocyanate groups was 4.1%, the number average molecular weight (Mn) was 2,600, and the content of alkaline metals and/or alkaline earth metals was 0.01 mmol/kg. The content of oxyethylene groups in the polyol component (B) was 60% by weight, and the content of oxyethylene groups in (UP) was 40% by weight.

Example 3

The medical adhesive (P3) of the present invention was obtained by the same method as that in Example 1, except using a mixture of 90 parts of the random co-adduct of ethylene oxide/propylene oxide (b1) obtained in Production Example 1 and 10 parts of the adduct of propylene oxide (b3) obtained in Production Example 3 as the polyol component (B) and 45.6 parts of bis(isocyanatomethyl)perfluorobutane [OCN—$CH_2$—$(CF_2)_4$—$CH_2$—NCO] (the ratio of NCO group/OH group=2/1) as the fluorine-containing nonaromatic polyisocyanate component (A). As for this (P3), the content of isocyanate groups was 4.0%, the number average molecular weight (Mn) was 5,400, and the content of alkaline metals and/or alkaline earth metals was 0.02 mmol/kg. The content of oxyethylene groups in the polyol component (B) was 72% by weight, and the content of oxyethylene groups in (UP) was 49% by weight.

Example 4

The medical adhesive (P4) of the present invention was obtained by the same method as that in Example 1, except using a mixture of 70 parts of the random co-adduct of ethylene oxide/propylene oxide (b1) obtained in Production Example 1 and 30 parts of the adduct of propylene oxide (b4) obtained in Production Example 4 as the polyol component (B), 61.0 parts of bis(isocyanatomethyl)perfluorobutane (the ratio of NCO group/OH group=2.2/1) as the fluorine-containing nonaromatic isocyanate component (A), and 0.8 parts of 1,1,3-tris(2-methyl-4-hydroxy-5-t-butylphenyl)butane (Adekastab AO-30, manufactured by Asahi Denka Co., Ltd.) as the phenolic radical scavenger (PRS). As for this (P4), the content of isocyanate groups was 5.6%, the number average molecular weight (Mn) was 2,300, and the content of alkaline metals and/or alkaline earth metals was 0.02 mmol/kg. The content of oxyethylene groups in the polyol component (B) was 56% by weight, and the content of oxyethylene groups in (UP) was 34% by weight.

Example 5

The medical adhesive (P5) of the present invention was obtained by the same method as that in Example 1, except using a mixture of 85 parts of the random co-adduct of ethylene oxide/propylene oxide (b2) obtained in Production Example 2 and 15 parts of the adduct of propylene oxide (b5) obtained in Production Example 5 as the polyol component (B), 45.4 parts of bis(isocyanatomethyl)perfluorohexane (the ratio of NCO group/OH group=1.9/1) as the fluorine-containing nonaromatic isocyanate component (A), and 0.3 parts of 1,3,5-tris(3',5'-di-t-butyl-4'-hydroxybenzyl)-sec-triazine-2,4,6-(1H,3H,5H)trion (Adekastab AO-20, manufactured by Asahi Denka Co., Ltd.) as the phenolic radical scavenger (PRS). As for this (P5), the content of isocyanate groups was 4.0%, the number average molecular weight (Mn) was 2,500, and the content of alkaline metals and/or alkaline earth metals was 0.02 mmol/kg. The content of oxyethylene groups in the polyol component (B) was 51% by weight, and the content of oxyethylene groups in (UP) was 47% by weight.

Comparative Example 1

The medical adhesive (C1) for comparison was obtained by the same method as that in Example 1, except that the phenolic radical scavenger {tetrakis-[methylene-3-(3',5'-di-t-butyl-4'-hydroxyphenyl) propionate]methane} was not added. As for this (C1), the content of isocyanate groups was 1.8%, the number average molecular weight (Mn) was 5,700, and the content of alkaline metals and/or alkaline earth metals was 0.03 mmol/kg.

Comparative Example 2

The medical adhesive (C2) for comparison was obtained by the same method as that in Example 4, except that the phenolic radical scavenger {1,1,3-tris(2-methyl-4-hydroxy-5-t-butylphenyl)butane} was not added. As for this (C2), the content of isocyanate groups was 5.5%, the number average molecular weight (Mn) was 2,400, and the content of alkaline metals and/or alkaline earth metals was 0.02 mmol/kg.

Comparative Example 3

The medical adhesive (C3) for comparison was obtained by the same method as that in Example 1, except that a phosphorous antioxidant {0.5 parts of tris(2,4-di-t-butylphenyl)phosphite (Adekastab 2112, manufactured by Adeka Argus Chemical Co., Ltd.)} was added in place of the phenolic radical scavenger {0.5 parts of tetrakis-[methylene-3-(3',5'-di-t-butyl-4'-hydroxyphenyl) propionate]methane}. As for this (C3), the content of isocyanate groups was 1.8%, the number average molecular weight (Mn) was 5,600, and the content of alkaline metals and/or alkaline earth metals was 0.03 mmol/kg.

Comparative Example 4

The medical adhesive (C4) for comparison was obtained by the same method as that in Example 1, except that an amine radical scavenger {0.2 parts of phenothiazine} was added in place of the phenolic radical scavenger {0.5 parts of tetrakis-[methylene-3-(3',5'-di-t-butyl-4'-hydroxyphenyl) propionate]methane}. As for this (C4), the content of isocyanate groups was 1.8%, the number average molecular weight (Mn) was 5,700, and the content of alkaline metals and/or alkaline earth metals was 0.03 mmol/kg.

Comparative Example 5

The medical adhesive (C5) for comparison was obtained by the same method as that in Example 1, except that 100 parts of the adduct of propylene oxide (b6) obtained in Production Example 6 was used as the polyol component (B), 0.5 parts of tetrakis-[methylene-3-(3',5'-di-t-butyl-4'-hydroxyphenyl) propionate]methane was added as the phenolic radical scavenger (PRS), and 17.6 parts of bis(isocyanatomethyl)perfluorobutane [OCN—$CH_2$—$(CF_2)_4$—$CH_2$—NCO] (the ratio of NCO group/OH group=2.2/1) was used as the fluorine-containing nonaromatic polyisocyanate component (A). As for this (C5), the content of isocyanate groups was 2.0%, the number average molecular weight (Mn) was 5,400, and the content of alkaline metals and/or alkaline earth metals was 0.01 mmol/kg. No oxyethylene group is contained in the polyol component (B) and (UP).

Comparative Example 6

100 parts of the random co-adduct of ethylene oxide/propylene oxide (b1) obtained in Production Example 1 was dehydrated under reduced pressure and nitrogen atmosphere at 100° C. for 2 hours, followed by cooling to 40° C. Then, 8.7 parts of 2,4-tolylenediisocyanate (TDI) (the ratio of NCO group/OH group=2/1) was added and the mixture was stirred uniformly. After heating to 80° C., the mixture was reacted at 80° C. for 6 hours and the medical adhesive (C6) for comparison was obtained. As for this (C6), the content of isocyanate groups was 1.9%, the number average molecular weight (Mn) was 5,600, and the content of alkaline metals and/or alkaline earth metals was 0.03 mmol/kg.

<Evaluation 1: Production of Product Cured by the Reaction with Water (a Cured Sheet for Evaluation) and Change in Appearance Thereof>

An adhesive for evaluation was coated on a glass plate into a thickness of 200 μm by the use of an applicator, and the coated glass plate was soaked in a water bath of 25° C. quietly. The adhesive for evaluation cured while foaming to form a sheet containing bubbles. 8 hours after being soaked in the water bath, the water-cured sheet was peeled off from the glass plate. After adhesive water on this water-cured sheet was wiped off, the water-cured sheet was cut into a size of 3 cm×5 cm and a product cured by the reaction with water (a cured sheet for evaluation) was obtained.

This product cured by the reaction with water was put on a glass plate and was let alone for 5 days in a constant temperature-bath where the temperature had been adjusted to 37° C. 5 days later, the appearance of this product cured by the reaction with water was visually observed and evaluated by the following standard. This evaluation result is shown in Table 1.

<Evaluation Standard>
Excellent: The sheet shape was maintained.
Poor: Part or all of the sheet have changed into viscous liquid (the sheet shape was not maintained).
*: Only the surface cured, and the inside was uncured and the foam sheet could not be formed.

<Evaluation 2: Wet Adhesive Strength>

After two pieces of collagen sheets were soaked in physiological saline for 24 hours, physiological saline of the surfaces of the collagen sheets was wiped off, and one collagen sheet was spread on a glass plate. About 0.1 mL of the adhesive for evaluation was applied on the area of 1 cm×1 cm on the edge part of this collagen sheet with the use of a spatula made of the silicone resin.

The 1 cm×1 cm area of the edge part of the other collagen sheet was pasted together on the area the adhesive for evaluation was applied, and a specimen was made. The weight of 100 g was put so as to apply the load of 100 g/cm$^2$ on the part pasted together of this specimen and let the specimen alone for 5 minutes under the environment of 37±2° C. and 95±5 RH % in humidity. After that, the weight was removed and the specimen peeled off from the glass plate was soaked in physiological saline of 37±2° C. for 5 minutes, and thus the collagen-bonded sheet was obtained. After that, drops of water attached to the collagen-bonded sheet were removed with gauze, and then the collagen-bonded sheet was put in a constant temperature- and constant humidity-bath adjusted to 37±2° C. and 95±5 RH % in humidity and let alone for 2 hours in order to obtain a test piece.

Next, according to JIS K6850-1999, tensile strength was measured under the environment of 37±2° C. and 95±5 RH % in humidity for the test piece, and the load when breaking was assumed to be wet adhesive strength 2H (kg/cm).

After another test piece was let alone for 5 days in a constant temperature- and constant humidity-bath of 37±2° C. and 95±5 RH % in humidity, the tensile strength was measured in the same way, and the load when breaking was assumed to be wet adhesive strength 5D (kg/cm) These wet adhesive strength 2H and 5D are shown in Table 1.

Autograph AGS-500B manufactured by Shimadzu Corporation was used as a tensile testing machine, and the pulling speed was made to be 300 mm/min. The parts to be fixed with the grip tool were made the edge part of 1 cm of the collagen sheet that did not allowed to be bonded and also the similar edge part of 1 cm of the other collagen sheet.

TABLE 1

|  | Example | | | | | Comparative Example | | | | | |
| --- | --- | --- | --- | --- | --- | --- | --- | --- | --- | --- | --- |
|  | 1 | 2 | 3 | 4 | 5 | 1 | 2 | 3 | 4 | 5 | 6 |
| Change in appearance | Excellent | Excellent | Excellent | Excellent | Excellent | Poor | Poor | Poor | Poor | * | Excellent |
| Wet adhesive strength (2H) | 1.2 | 1.1 | 1.4 | 1.4 | 1.4 | 1.1 | 1.4 | 1.2 | 1.1 | — | 0.9 |
| Wet adhesive strength (5D) | 1.3 | 1.2 | 1.4 | 1.3 | 1.4 | — | — | — | — | — | 0.8 |

As for change in the appearance, the cured sheets for evaluation obtained from the medical adhesives (P1) to (P5) of the present invention maintained the sheet shapes. The sheets did not break even if they were lightly pulled by hands. On the other hand, the cured sheets for evaluation obtained from the medical adhesives (C1) to (C4) for comparison changed into viscous liquid on the glass plates. There were not signs of the sheet shape any longer either.

As for wet adhesive strength, all of the medical adhesives (P1) to (P5) of the present invention showed extremely excellent wet adhesive strength both at 2 hours later and 5 days later. On the other hand, though the medical adhesives (C1) to (C4) for comparison showed wet adhesive strength equal with the adhesive of the present invention at 2 hours later, the wet adhesive strength could not be measured at 5 days later because part of the bonded place changed into viscous liquid (represented by "—").

As for medical adhesive (C5) for comparison, the sheet could not be made in evaluation 1 (8 hours after being soaked in the water bath, the water-cured sheet was tried to be peeled off from the glass plate, but it could not be peeled off in sheet-like, and it became apart.) In evaluation 2, when the specimen was tried to peel off from the glass plate, the bonded part of the collagen sheet was peeled off to divide into two pieces of collagen sheet (it is estimated that the wet adhesive strength is less than 0.1 in the measurement limit.)

Though the evaluation results of medical adhesive (C6) for comparison were equal with the medical adhesive of the present invention both in change in the appearance and in the wet adhesive strength 2H and 5D, TDI, which is the aromatic isocyanate, is contained in this adhesive (C6) as a constitutional unit, and it is thought that there is a problem in the point of safety (mutagenicity and the like).

<Evaluation 3: Evaluation of In Vivo Hemostatic Capability>

The carotid arteries (about 4 mm in outside diameter) of three adult dogs under anesthesia were exposed, and about 6 cm in length of the carotid arteries were separated. After heparinization, blood vessel was temporarily clamped by the use of two blood vessel-forcipes, and the carotid artery was cut between two forcipes. The edges of the cut carotid artery were anastomosed at four places (top and bottom, and right and left) with the suture, and the medical adhesive (P3) of the present invention was applied on all surroundings of anastomosis site and let alone for 5 minutes. After that, the forcipes of both sides were opened, and when the existence or absence of bleeding was observed, bleeding was completely stopped for all of the three dogs. The average systolic blood pressure was 178 mmHg and the average diastolic blood pressure was 88 mmHg after the stop of bleeding. The parts where the adhesive of the present invention had cured were enough flexible, these parts and anastomosis site were pulsatory. Though the activated clotting time (ACT) of the blood before heparin was administered was 121 seconds on the average, it was 1,000 seconds or more and could not be measured (the blood did not coagulate) during the experiment after the administration of heparin, and it was clear that the stop of bleeding in this experiment was not due to the coagulation of blood.

After sacrificing two dogs among the three dogs, the anastomosis sites where the carotid arteries were excised were observed. No sign that the adhesive intruded into the lumens was recognized.

The other one was bred for three months, and the angiography and the anatomical observation were conducted. The stenosis in the anastomosis site was not observed by the angiography inspection. According to the anatomical opinion after three months of the operation, though the cured product of the adhesive of the present invention covered the anastomosis site and remained as a gell-like material, the blood vessel in the anastomosis site was healed completely.

INDUSTRIAL APPLICABILITY

Though the medical adhesive of the present invention reacts with water in the body fluid such as blood, there is no deterioration and decomposition with the passage of time for the product cured by the reaction with water. Therefore, the excellent adhesive strength thereof can be maintained for a long period. The medical adhesive of the present invention can be particularly used effectively for bonding body tissues with movement in particular. The medical adhesive of the present invention is extremely effective as a medical adhesive used for, for example, bonding of lung, artery, heart, vein, trachea, esophagus, stomach, duodenum, small intestine, colon, rectum, liver, spleen, kidney, pancreas and nerves etc., stopping bleeding, preventing the leakage of digestive juice from digestive organs, temporarily fixing before suturing, reinforcing the diseased part, and the like, and further exhibits high reliability and high capability for joining the surface of a wound, an incision wound part, and the like, and bonding treatment in the dental surgery. The medical adhesive of the present invention exhibits particularly high reliability and capability in bonding of the tissue that moves, such as artery and heart in particular.

Further, the medical adhesive of the present invention shows especially remarkable effect as the hemostatic sealant for a bleeding site, besides as the adhesive for bonding body tissues. Especially, even in a surgical operation of heart or aorta that uses an artificial heart-lung machine and is conducted under the administration of an anticoagulant, the spurting bleeding can be suppressed in a short period of time by the medical adhesive of the present invention.

The invention claimed is:
1. A medical adhesive which comprises a hydrophilic urethane prepolymer (UP) obtained by reacting a fluorine-containing aliphatic diisocyanate (A11) having 5 to 12 carbon atoms and a polyol component (B) having a hydrophilic polyol (B1), and a phenolic radical scavenger (PRS), and
    the fluorine-containing aliphatic diisocyanate (A11) is a diisocyanate represented by OCN—$CH_2$—Rf—$CH_2$—NCO, wherein Rf represents a perfluoroalkylene group having 3 to 10 carbon atoms, which optionally contains an ether bond,
    a content of oxyethylene groups in the polyol component (B) is 30 to 100% by weight based on the weight of oxyalkylene groups in (B),
    the hydrophilic polyol (B1) is a polyether polyol (B1-1),
    the polyether polyol (B1-1) is an adduct of ethylene oxide, or a co-adduct of ethylene oxide and alkylene oxide having 3 to 8 carbon atoms to a compound having at least two active hydrogens,
    an equivalent weight of the hydroxyl group in the hydrophilic polyol (B1) is from 50 to 5,000,
    the phenolic radical scavenger (PRS) is at least one selected from the group consisting of 2,6-di-t-butyl-p-cresol, butylated hydroxyanisole, 2,6-di-t-butyl-4-ethylphenol, stearyl-β-(3,5-di-t-butyl-4-hydroxyphenyl)propionate, 2,2'-methylenebis (4-methyl-6-t-butylphenol), 2,2'-methylenebis (4-ethyl-6-t-butylphenol), 4,4'-butylidenebis (3-methyl-6-t-butylphenol), 4,4'-thiobis (3-methyl-6-t-butylphenol), 1,6-hexanediol-bis[3-(3,5-di-t-butyl-4-hydroxyphenyl)propionate], 3,9-bis[1,1-dimethyl-2-[β-(3-t-butyl-4-hydroxy-5-methylphenyl)propionyl]ethyl]2,4,8,10-tetraoxaspiro[[5,5]]undecane, tetrakis-[methylene-3-(3',5'-di-t-butyl-4'-hydroxyphenyl)propionate]methane, 1,3,5-trimethyl-2,4,6-tris(3,5-di-t-butyl-4-hydroxybenzyl)benzene, 1,1,3-tris(2-methyl-4-hydroxy-5-t-butylphenyl)butane, bis[3,3'-bis-(4'-hydroxy-3'-t-butylphenyl)butylic acid]glycol ester, and 1,3,5-tris(3',5'-di-t-butyl-4'-hydroxybenzyl)-sec-triazine-2,4,6-(1H,3H,5H) trion, and
    a content of sodium, potassium and magnesium is between 0 to less than 0.04 mmol/kg based on the weight of (UP).
2. The medical adhesive according to claim 1 wherein the content of the phenolic radical scavenger (PRS) is 0.01 to 3% by weight based on the weight of (UP).
3. The medical adhesive according to claim 1 wherein the polyol component (B) contains a mixture of a random copolymer obtained by addition of ethylene oxide and propylene oxide to diols and polypropylene glycol.
4. The medical adhesive according to claim 1 wherein a content of isocyanate groups in the medical adhesive is 1 to 10% by weight based on the weight of (UP).
5. The medical adhesive according to claim 1 which has a viscosity (at 37° C.) of 0.5 to 500 Pa·s, a maximum amount of water absorption of 0.2 to 5 ml/g, an initial rate of water absorption of 0.01 to 0.5 ml/g·min, and a content of oxyethylene groups in the hydrophilic urethane prepolymer (UP) of 30 to 100% by weight based on the weight of the oxyalkylene groups in (UP), and forms into a film having a wet 100% modulus of 0.01 to 10 MPa after cured.
6. A hemostatic sealant which comprises the medical adhesive according to claim 1.
7. A method for bonding body tissues using the medical adhesive according to claim 1, comprising an application step of applying the medical adhesive on an incised body part, wherein the application step is:

a direct application step in which the medical adhesive is directly applied on the incised part; or a transcription application step in which the medical adhesive is applied on a film, then the incised part is covered with the film, and then the film is removed after a reaction of the medical adhesive.

8. The method for bonding body tissues according to claim 7 wherein the body tissue is at least one tissue selected from the group consisting of blood vessel, heart, respiratory organ and digestive organ.

* * * * *